US011123078B2

(12) United States Patent
Gruba et al.

(10) Patent No.: US 11,123,078 B2
(45) Date of Patent: Sep. 21, 2021

(54) DELIVERY AND OCCLUSION DEVICES FOR PARAVALVULAR LEAK

(71) Applicants: Boston Scientific Scimed, Inc., Maple Grove, MN (US); Mayo Foundation for Medical Education and Research, Rochester, MN (US)

(72) Inventors: Sarah M. Gruba, Vadnais Heights, MN (US); Katherine L. Baldwin, Minneapolis, MN (US); James P. Rohl, Prescott, WI (US); Todd College, Little Canada, MN (US); Charanjit S. Rihal, Rochester, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 164 days.

(21) Appl. No.: 16/122,623

(22) Filed: Sep. 5, 2018

(65) Prior Publication Data

US 2019/0159785 A1    May 30, 2019

Related U.S. Application Data

(60) Provisional application No. 62/593,167, filed on Nov. 30, 2017.

(51) Int. Cl.
*A61F 2/24* (2006.01)
*A61B 17/12* (2006.01)
(Continued)

(52) U.S. Cl.
CPC ...... *A61B 17/12122* (2013.01); *A61F 2/2427* (2013.01); *A61B 1/00* (2013.01);
(Continued)

(58) Field of Classification Search
CPC .................................. A61F 2/24; A61B 17/12
See application file for complete search history.

(56) References Cited

U.S. PATENT DOCUMENTS 8,287,584 B2    10/2012    Salahieh et al.
8,961,556 B2     2/2015    Amplatz et al.
(Continued)

FOREIGN PATENT DOCUMENTS

| CN | 206586978 U | 10/2017 |
|---|---|---|
| EP | 2572644 A1 | 3/2013 |
| WO | 2016192781 A1 | 12/2016 |

OTHER PUBLICATIONS

Dellimore, K.H., et al., "A Review of Catheter Related Complications During Minimally Invasive Transcatheter Cardiovascular Intervention with Implications for Catheter Design", 5(3):217-232 (2014).
(Continued)

*Primary Examiner* — Matthew W Schall
(74) *Attorney, Agent, or Firm* — Kacvinsky Daisak Bluni PLLC

(57) ABSTRACT

The present disclosure relates generally to apparatuses and methods for delivering an occlusion device to a paravalvular leak. In some embodiments, a paravalvular occlusion apparatus includes a catheter having main body including a proximal end and a distal end, a visualization element disposed in the distal end of the main body, and a working channel extending from the distal end of the main body. The catheter further includes an elongate shaft extendable from the working channel, wherein an occlusion device is coupled to the elongate shaft. In some embodiments, an occlusion device includes a leading end including a first section, and a trailing end opposite the leading end, the trailing end including a second section. The first section and the second section of the occlusion device are operable to be positioned
(Continued)

along a perimeter of a prosthetic valve for blocking the paravalvular leak.

20 Claims, 11 Drawing Sheets

(51) Int. Cl.
*A61B 17/00* (2006.01)
*A61B 17/122* (2006.01)
*A61B 1/00* (2006.01)
*A61B 1/05* (2006.01)
*A61B 17/128* (2006.01)
*A61B 1/06* (2006.01)

(52) U.S. Cl.
CPC ............... *A61B 1/05* (2013.01); *A61B 1/0676* (2013.01); *A61B 17/1227* (2013.01); *A61B 17/1285* (2013.01); *A61B 17/12136* (2013.01); *A61B 17/12172* (2013.01); *A61B 2017/00243* (2013.01); *A61B 2017/00314* (2013.01); *A61B 2017/00557* (2013.01); *A61B 2017/00783* (2013.01); *A61B 2017/00867* (2013.01); *A61B 2017/1205* (2013.01); *A61F 2/246* (2013.01); *A61F 2/2466* (2013.01); *A61F 2210/0014* (2013.01); *A61F 2230/001* (2013.01); *A61F 2230/0039* (2013.01); *A61F 2250/0003* (2013.01); *A61F 2250/0069* (2013.01); *A61F 2310/00011* (2013.01)

(56) References Cited

U.S. PATENT DOCUMENTS

| | | | |
|---|---|---|---|
| 2006/0004442 | A1 | 1/2006 | Spenser et al. |
| 2009/0062841 | A1 | 3/2009 | Amplatz et al. |
| 2009/0112311 | A1 | 4/2009 | Miles et al. |
| 2010/0004679 | A1 | 1/2010 | Osypka |
| 2011/0046662 | A1 | 2/2011 | Moszner et al. |
| 2014/0277426 | A1 | 9/2014 | Dakin et al. |
| 2016/0213228 | A1* | 7/2016 | Rohl .................. A61B 17/0401 |
| 2016/0256268 | A1 | 9/2016 | Dakin |
| 2016/0367120 | A1 | 12/2016 | Dupont et al. |
| 2018/0133442 | A1 | 5/2018 | Adriaens et al. |

OTHER PUBLICATIONS

Benoit, R., et al., "Cardioscopically Guided Beating Heart Surgry: Paravalvular Leak Repair", The Annals of Thoracic Surgery 104(3):1074-1079 (2017).

International Search Report and Written Opinion for International application No. PCT/US2018/049586, dated Jan. 24, 2019, 16 pages.

* cited by examiner

DELIVERY AND OCCLUSION DEVICES FOR PARAVALVULAR LEAK

CROSS REFERENCE TO RELATED APPLICATION

This application claims priority to U.S. provisional patent application Ser. No. 62/593,167, filed Nov. 30, 2017, the entire contents of which is incorporated by reference herein.

FIELD

The present disclosure relates generally to the field of occlusion devices and, more particularly, to occlusion devices and delivery systems for addressing a paravalvular leak.

BACKGROUND

A paravalvular or paraprosthetic leak (PVL) is a complication associated with the implantation of a prosthetic heart valve. PVLs have commonly been observed in patients surgically implanted with either bioprosthetic or mechanical valves. PVL refers to blood flowing through a channel between the structure of the implanted valve and cardiac tissue as a result of a lack of appropriate sealing. Some PVLs are crescent, oval or roundish-shaped, and their track can be parallel, perpendicular or serpiginous. PVL may be caused by several factors including suture dehiscence, weak tissue, improper valve sizing, and others. This leak may cause symptoms of heart failure and hemolytic anemia.

One current approach to address PVLs requires a wire to be threaded through the leak from the atrium. The wire is then snared in the ventricle to hold it in place. A vascular plug may then be placed into the PVL via the wire. However, this type of procedure has the potential for difficulties throughout the entire surgery, as the procedure is challenging and time consuming. Notably, the step of placing the wire into the PVL can take anywhere from minutes to hours depending on the skill of the operator, the size/shape of the PVL, and the back-flow pressure.

A variety of advantageous medical outcomes may therefore be realized by the device and/or methods of the present disclosure, which provide delivery of an occlusion device for a PVL.

SUMMARY

The present disclosure in its various embodiments relates generally to devices and methods for occlusion devices and delivery systems for addressing a paravalvular leak. In one or more embodiments, a paravalvular occlusion apparatus may include a catheter having a main body with a proximal end and a distal end, a visualization element disposed in the distal end of the main body, and a working channel extending from the distal end of the main body. The catheter may further include an elongate shaft extendable from the working channel. The paravalvular occlusion apparatus may further include an occlusion device coupled to the elongate shaft, the occlusion device including a leading end having a first section, and a trailing end opposite the leading end, the trailing end including a second section, wherein the first section and the second section are operable to be positioned along a perimeter of an artificial valve. The occlusion device may further include a connector element extending between the first and second sections. A diameter length of the connector element may be less than a diameter length of at the first section or the second section. The occlusion device may further include an internal frame disposed within at least one of the first section, the second section, or the connector element. The internal frame may be a nitinol braided frame extending throughout the first section, the second section, and the connector element. The internal frame of the occlusion device may be connected to a connection joint extending from the second section, wherein the connection joint is coupled with the elongate shaft of the catheter. The catheter may further include a balloon extending around the working channel. The first and second sections of the occlusion device may have one of the following shapes: circular, elliptical, square, or crescent. A shape of the first section of the occlusion device may be different than a shape of the second section of the occlusion device. The first section of the occlusion device may have an interior concave surface operable to abut an exterior surface of a stent of the artificial valve. The second section of the occlusion device may be operable to extend over the perimeter of the artificial valve and partially along an outer surface of one or more leaflets of the artificial valve. The paravalvular occlusion apparatus may further include one or more additional occlusion devices positionable along the perimeter of the artificial valve. The occlusion device may be in direct physical abutment with the one or more additional occlusion devices. The occlusion device may further include one or more layers of an electro spun material. The first section of the occlusion device may have a crescent shape and the second section of the occlusion device has a disc shape.

In one or more embodiments, a paravalvular occlusion apparatus may include a catheter having a main body having a proximal end and a distal end, and a visualization element disposed in the distal end of the main body. The catheter may further include a working channel extending from the distal end of the main body, and an elongate shaft extendable from the working channel. The paravalvular occlusion apparatus may further include an occlusion device coupled to the elongate shaft, the occlusion device having a leading end including a first section, and a trailing end opposite the leading end, wherein the trailing end includes a second section, and wherein the first section and the second section are operable to be positioned along a perimeter of an artificial valve in an area of a paravalvular leak. The occlusion device may further include a connector element extending between the first and second sections. The occlusion device may further include an internal frame disposed within at least one of: the first section, the second section, and the connector element.

In one or more embodiments, a method for delivering an occlusion device to a paravalvular leak may include advancing a catheter in a body of patient to a paravalvular leak. The catheter may include a main body having a proximal end and a distal end, a visualization element disposed in the distal end of the main body, a working channel extending from the distal end of the main body, and an elongate shaft extendable from the working channel. The method may further include delivering an occlusion device from the working channel of the catheter. The occlusion device may include a leading end including a first section, and a trailing end opposite the leading end, the trailing end including a second section connected to the first section by a connector element, wherein the first section and the second section are operable to be positioned along a perimeter of a prosthetic valve. The method may further include positioning the working channel over the paravalvular leak using the visualization element. The method may further include deploying the occlusion device to the paravalvular leak by positioning the occlusion device in abutment with the perimeter of the prosthetic valve, and verifying a position of the occlusion device using the visualization element. The method may further include positioning an interior concave surface of the first section of the occlusion device directly against an exterior surface of a stent of the prosthetic valve, positioning the second section of the occlusion device partially over an outer surface of one or more leaflets of the prosthetic valve, and detaching the occlusion device from the catheter after positioning of the first and second sections relative to the prosthetic valve. The method may further include providing an internal frame of the occlusion device, the internal frame being connected to a connection joint extending from the second section, wherein the connection joint is coupled with the elongate shaft of the catheter. The method may further include positioning one or more additional occlusion devices along the perimeter of the prosthetic valve.

Various one or more of the features summarized above may be interchanged, exchanged, combined or substituted with or for other features summarized above, for use in connection with the medical systems and methods summarized above, and with respect to the embodiments described in greater detail below and embodiments otherwise within the scope of the present disclosure.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
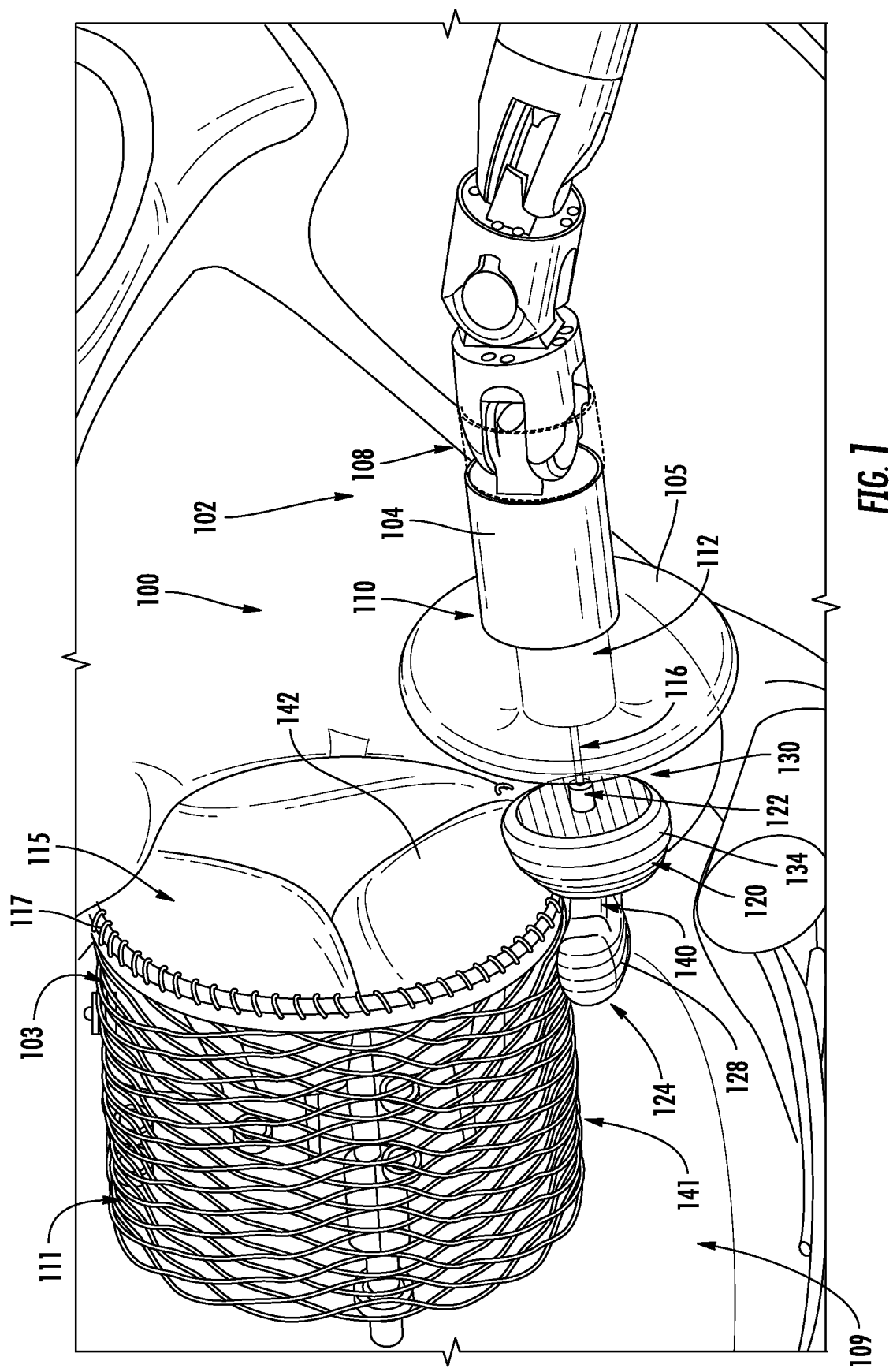
FIG. 1 is a side perspective view of an apparatus including a delivery device and occlusion device according to embodiments of the present disclosure.

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Embodiments herein disclose delivery devices including a direct visualization system to place an occlusion device at a desired location along an artificial or prosthetic valve (e.g., a heart valve), such as at the location of a leak. Embodiments herein also disclose occlusion devices shaped to conform to the leak shape, without pushing out the vasculature wall. Both the delivery device and occlusion device may be made of nitinol. Furthermore, the occlusion device may be covered in an electrospun material (e.g., chronoflex, polyisobutylene (PIB), polyurethane (PUR), poly(vinylidene fluoride) (PVDF), polycaprolactone (PCL), or poly(lactide-co-glycolid-es) (PLGA)) to help with endothelialization over the occlusion device and to impede blood flow back into the atrium.

The present disclosure relates generally to an apparatus and methods for delivering an occlusion device to a paravalvular leak. In some embodiments, a paravalvular occlusion apparatus includes a catheter having main body having a proximal end and a distal end, a visualization element disposed in the distal end of the main body, and a working channel extending from the distal end of the main body. The catheter may further include an elongate shaft extendable from the working channel, wherein an occlusion device is coupleable to the elongate shaft. The occlusion device includes a leading end having a first section, and a trailing end opposite the leading end, the trailing end having a second section. The first section and the second section of the occlusion device are operable to be positioned along a perimeter of a prosthetic valve for blocking the paravalvular leak.

As will be described in greater detail below, during use, the catheter may be brought into position using the visualization element to align the working channel with the location of the leak. It will be appreciated that the catheter may also be compatible with traditional imaging techniques, such as echocardiography, fluoroscopy, etc. The occlusion device may then be delivered from the working channel into the leak along the artificial valve. More specifically, the occlusion device is delivered to the leak by positioning the occlusion device in abutment with the perimeter of the prosthetic valve. The position of the occlusion device may then be verified, e.g., using the visualization element. One or more additional occlusion devices may similarly be delivered from the catheter.

Various embodiments herein may include a catheter having a balloon extending around the working channel and the second section. Various embodiments herein may include occlusion devices having one of the following shapes: circular, elliptical, square, and crescent. In some examples, a shape of the first section of the occlusion device is different than a shape of the second section of the occlusion device. In other examples, the shapes of the first and second sections are the same. In some embodiments, the first section of the occlusion device has an interior concave surface operable to abut an exterior surface of a stent of the artificial valve. Meanwhile, the second section of the occlusion device may be operable to extend over the perimeter of the artificial valve and partially along an outer surface of one or more leaflets of the artificial valve.

In various embodiments, one or more additional occlusion devices may also be positionable along the perimeter of the artificial valve, wherein the one or more additional occlusion devices may be in direct physical contact with the occlusion device. The occlusion device may further include an internal frame disposed within at least one of: the first section, the second section, and the connector element. The internal frame of the occlusion device may be connected to a connection joint extending from the second section, wherein the connection joint is coupled with the elongate shaft of the catheter.

Figure 2:
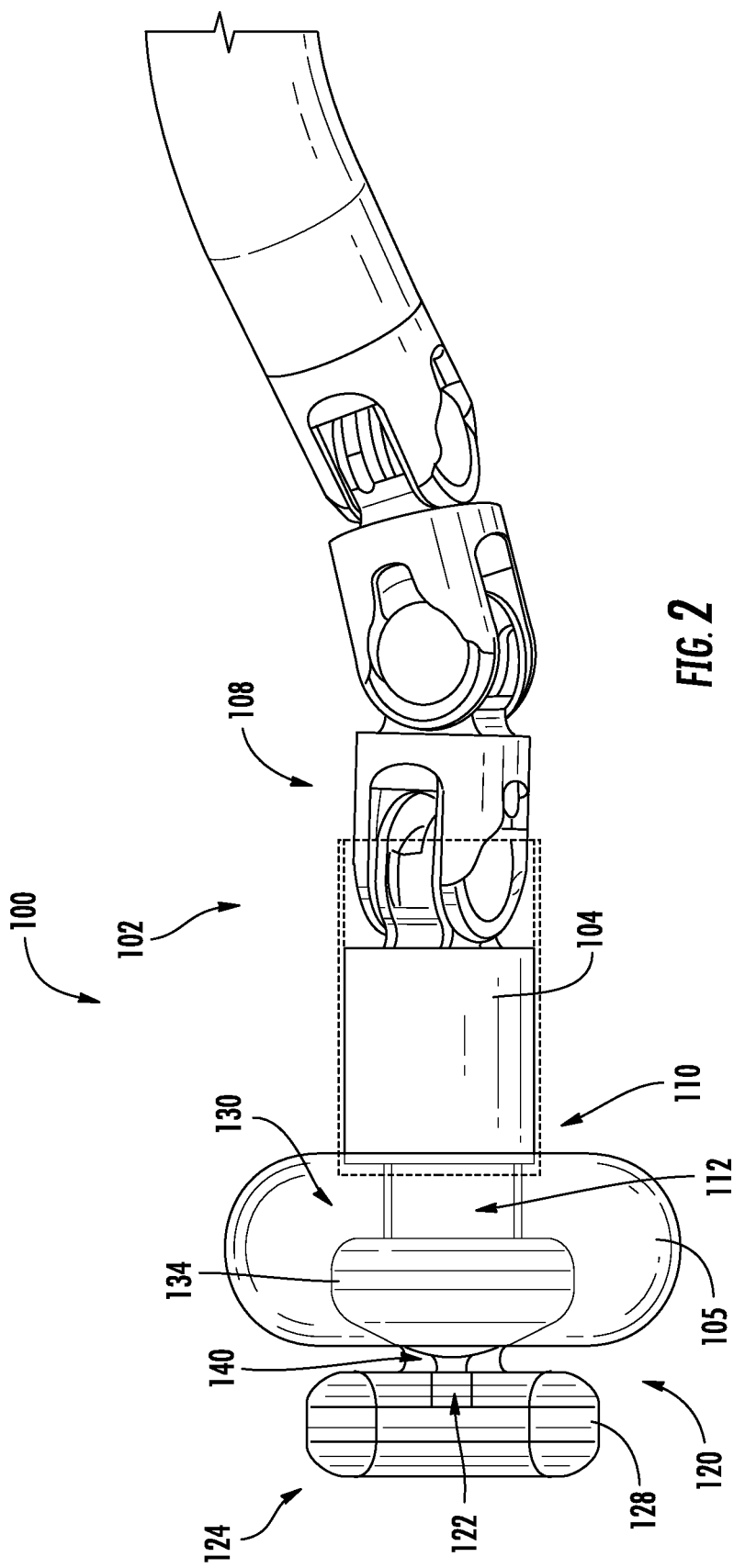
FIG. 2 is a side view of the apparatus of FIG. 1 according to embodiments of the present disclosure.
Figure 3:
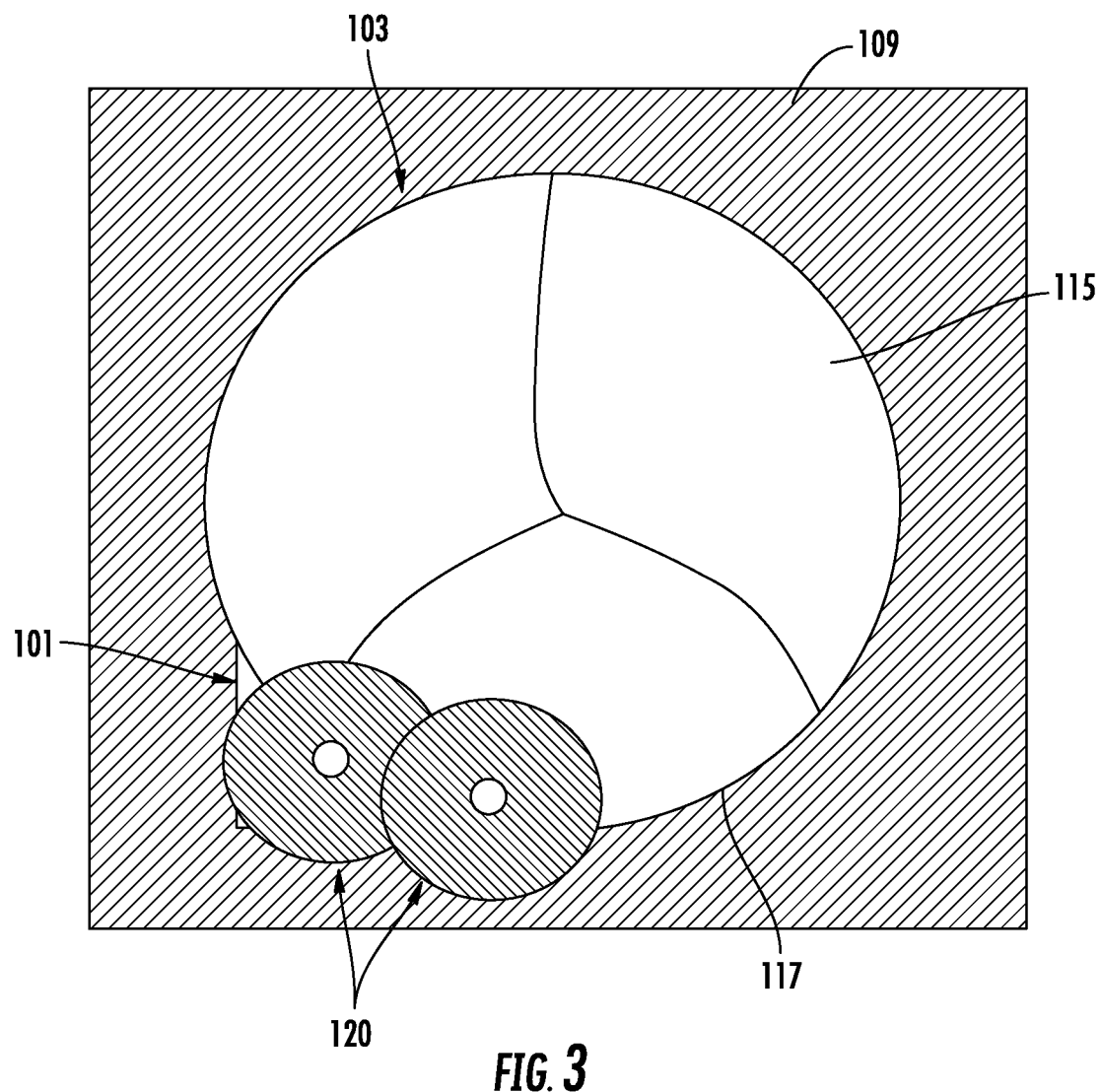
FIG. 3 is an end view of an artificial or prosthetic valve and occlusion devices according to embodiments of the present disclosure.

Turning now to FIGS. 1-3, a paravalvular occlusion apparatus (hereinafter "apparatus") 100 according to embodiments of the disclosure will be described in greater detail. FIG. 1 demonstrates a perspective view of the apparatus 100 during use within a patient, FIG. 2 demonstrates a side view of the apparatus 100 outside of a patient, while FIG. 3 demonstrates an end view of an artificial valve and implanted occlusion device(s) following retraction of a delivery device. As shown, the apparatus 100 includes a delivery device such as a catheter 102 for delivering an occlusion device 120 to a paravalvular leak 101 formed between one or more areas of tissue 109 and a prosthetic or artificial valve (hereinafter "valve") 103. The catheter 102 may have a main body 104 with a proximal end 108 and a distal end 110, wherein the distal end 110 includes a working channel 112 extending therefrom. The working channel 112 contains an elongate shaft 116 extendable from a center cavity of the working channel 112, the elongate shaft 116 being coupled to the occlusion device 120 by a connection joint 122.

As shown, a balloon 105 may be provided around the working channel 112, the balloon 105 shaped to conform to an atrial or ventricular wall surrounding the valve 103. Although not limited to any particular type of balloon, in some embodiments the balloon 105 can be a weeping balloon. A weeping balloon, in the context of the present disclosure, includes a balloon structure defining one or more perforations (also described as apertures or micropores, extending through a balloon wall). As such, weeping balloons can transfer inflation media through the balloon wall, from interior cavity to exterior surface of the balloon 105. Transferring inflation media to exterior surface can provide a benefit of displacing blood from an exterior surface of balloon 105 that would otherwise blur or obstruct visual imaging through the balloon 105. In other words, inflation media transferred through the one or more perforations can help keep the exterior surface visually clear. If a balloon is simply placed against an anatomical surface, blood can be trapped on the balloon surface and thus obscure the view. Inflation media (e.g., saline) exiting the pores of a weeping balloon can wash away this blood on the balloon surface adjacent to the wall. In some cases, a weeping balloon used in a balloon catheter visualization system or device provided herein can have at least 3 punctured holes. In some cases, weeping balloons used in balloon catheter visualization systems or devices provided herein can have between 3 and 10,000 puncture holes, between 3 and 1,000 puncture holes, between 3 and 100 puncture holes, or between 3 and 10 puncture holes. In some cases, the number and dimensions of puncture holes in a weeping balloon used in a balloon catheter visualization system or device provided herein allows for an inflation media flow rate of between 1 and 50 ml/minute. In some cases, systems and methods provided herein control an inflation media flow rate to be between 3 ml/minute and 10 ml/minute. In some cases, a weeping balloon used in balloon catheter visualization systems and devices provided herein can have hundreds of holes that perfuse inflation media (e.g., saline) through the balloon and into the blood. In some cases, a weeping balloon used in a balloon catheter visualization system or device provided herein can have a greater pore density in portions of the balloon wall in the center of the field of view and a lower pore density around a periphery of the field of view.

The balloon 105 can be constructed from various forms, e.g., a film, sheet or tube of transparent materials. Also, the balloon 105 may be formed into a variety of different shapes. FIGS. 1-2 shows an example of a donut-shaped balloon 105 having a thru lumen, i.e., the working channel 112, which can be sized and shaped to allow blood or other medical devices, such as the occlusion device 120, to pass therethrough. The balloon 105 is moveable between a collapsed or deflated state for navigation of the balloon 105 to or from the treatment site to an expanded or inflated state at the treatment site, especially if delivered within an introducer sheath. To move the balloon 105 from a collapsed state to an expanded state, a fluid may be added to the balloon 105. The balloon may be moved from an expanded state to a collapsed state by withdrawing fluid from the balloon 105. The medium used to inflate the balloon 105 may also be optically transparent and yet ideally be fluoroscopically opaque for navigation purposes. Suitable inflation medium may include a fluid such as saline or deionized water.

In some embodiments, the valve 103 includes an expandable stent 111, which may be formed from, for example, a shape-memory material, such as the nickel-titanium alloy known as "Nitinol" or other suitable metals. The stent 111 may be coupled to a plurality of leaflets 115 at a cuff or perimeter 117. The plurality of leaflets 115 collectively function as a one-way valve by coapting with one another. As a prosthetic aortic valve, the valve 103 may have three leaflets in some embodiments. However, it will be appreciated that other prosthetic heart valves with which the occlusion device 120 of the present disclosure may be used may have a greater or lesser number of leaflets 115. Both the perimeter 117 and the leaflets 115 may be wholly or partly formed of any suitable biological material or polymer such as, for example, polytetrafluoroethylene (PTFE).

Although not limited herein, the valve 103 may be used to replace a native aortic valve, a surgical heart valve or a heart valve that has undergone a surgical procedure. The valve 103 may be delivered to the desired site (e.g., near the native aortic annulus) using any suitable delivery device. During delivery, the valve 103 may be disposed inside the delivery device in the collapsed condition. The delivery device may be introduced into a patient using a transfemoral, transapical, transseptal or any other percutaneous approach. Once the delivery device has reached the target site, the user may deploy the valve 103. Upon deployment, the valve 103 expands so that an annulus section is in secure engagement within the native aortic annulus. When the valve 103 is properly positioned inside the heart, it may work as a one-way valve, allowing blood to flow from the left ventricle of the heart to the aorta, and preventing blood from flowing in the opposite direction.

The occlusion device 120 includes a leading end 124 including a first section 128, and a trailing end 130 opposite the leading end 124, the trailing end 130 including a second section 134. As shown, the leading end 124 may be considered a distal end of the occlusion device 120, while the trailing end 130 may be considered a proximal end of the occlusion device 120. A connector element 140 may extend between the first section 128 and the second section 134, wherein a diameter length of the connector element 140 is less than a diameter length of the first and/or second sections 128, 134. The first section 128 and the second section 134 of the occlusion device 120 are operable to be positioned along the perimeter 117 of the valve 103 for blocking the paravalvular leak 101. More specifically, once positioned against the valve 103, an interior surface of the first section 128 is operable to extend along an exterior surface 141 of the stent 111. Meanwhile, the second section 134 is operable to extend over the perimeter 117 of the valve 103 and partially along an outer surface 142 of an adjacently located leaflets 115. In some embodiments, the connector element 140 may be in direct abutment with the perimeter 117 of the valve 103. In the case where multiple occlusion devices 120 are present, for example as shown in FIG. 3, the occlusion devices 120 may be in direct physical contact with one another. Alternatively, each of the occlusion devices 120 may be spaced apart at different positions along the perimeter 117, as desired, depending on the number and location of paravalvular leaks.

The occlusion device 120 may be delivered percutaneously by the catheter 102, e.g., via femoral artery, jugular, or ported graft. In percutaneous embodiments, a camera may be connected to or associated with a catheter delivery system for a percutaneous delivery of the occlusion device 120, so that a user may verify a desired location, as will be described in greater detail below. In other embodiments, the occlusion device 120 may be delivered to the valve 103 surgically, for example, as described in co-pending application filed concurrently, entitled "Connected Anchor Delivery System and Method for Valve Repair,", which is herein incorporated by reference in its entirety. With a surgical delivery, such as open-heart surgery or open access surgery, and/or ported surgery, a sheath (not shown) may be used to deliver the occlusion device 120 to the paravalvular leak.

Turning now to FIGS. 4A-E, various occlusion devices 420 will be described in greater detail. Each of the occlusion devices may include a covering material, which may be made from an electrospun material (e.g., chronoflex, PIB PUR, PVDF, PCL, or PLGA) to help with endothelialization over the occlusion device and impede blood flow back into the atrium. Each of the occlusion devices 420 may be a conformable occluder intended to fill irregularities between the valve 103 and the tissue 109 (FIG. 1 and FIG. 3), while affording a low radial outward force. Thus, the occlusion devices 420 may be flexible and capable of contracting in the radial direction when a force is applied thereto to conform to the shape of the annulus in which it will be implanted. Moreover, the ability of occlusion devices 420 to longitudinally stretch will allow the occlusion devices to be delivered through a small diameter catheter. Although not shown, the occlusion devices 420 may operate with a detachable wire so that the occlusion devices 420 may be released and permanently placed within a patient.

In various other embodiments, the covering material employed in the embodiments shown in FIGS. 4A-E, as well as other embodiments described herein (see, e.g., FIGS. 5A-G described below), may be made of any flexible, biocompatible material capable of acting as a barrier to fluid flow (e.g., blood emerging from the orifice of a heart valve). Such covering materials can include, but are not limited to, polymeric films and fabrics including polyesters such as polyethylene terephthalate, fluoropolymers such as polytetrafluoroethylene (PTFE) and expanded polytetrafluoroethylene (ePTFE), polyamides, including nylon, polyether block amides (e.g., PEBAX), chemical vapor deposited polyxylylene polymers (parylenes) including poly(p-xylylene) polymers, polysiloxanes including silicone, polyurethanes, including thermoplastic polyurethanes (TPU), such as polyether polyurethanes, polyisobutylene-polyurethanes, polyurethane-silicone copolymers, poly(vinylidene fluoride-hexafluoropropylene) (PVDF-HFP), polyisobutylene copolymers including polyisobutylene-polystyrene block copolymers such as polystyrene-polyisobutylene-polystyrene triblock copolymers (SIBS), as well as metallic films, or combinations of the foregoing materials.

Figure 4A:
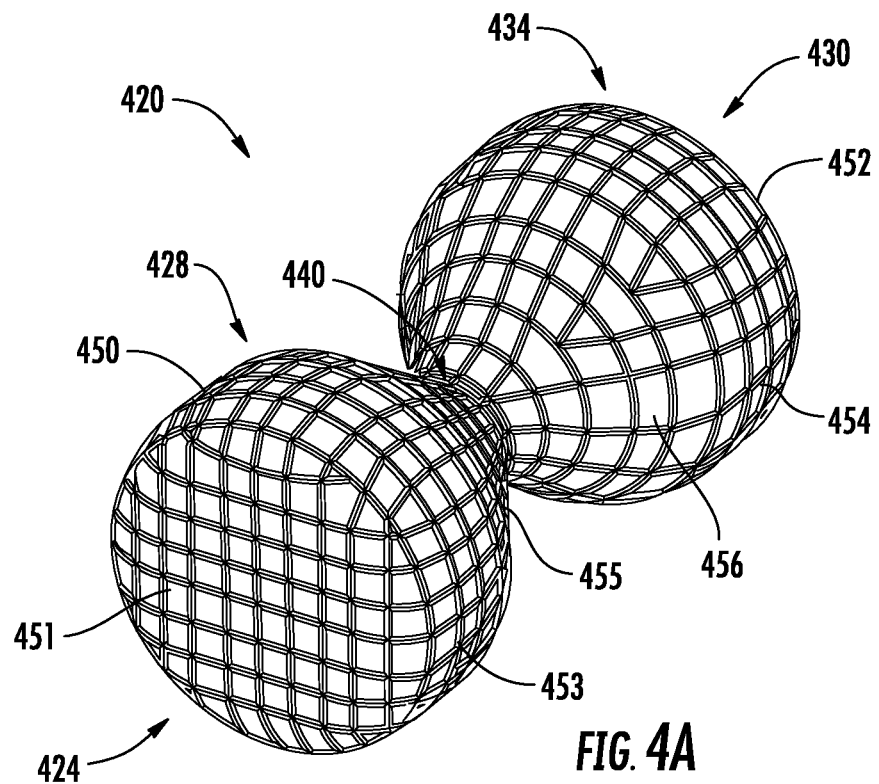
FIGS. 4A-E are perspective views of various occlusion devices according to embodiments of the present disclosure.

As shown in FIG. 4A, the occlusion device 420 includes a leading end 424 including a first section 428, and a trailing end 430 opposite the leading end 424, the trailing end 430 including a second section 434. A connector element 440 extends between the first section 428 and the second section 434. The first section 428 and the second section 434 of the occlusion device 420 are operable to be positioned along the perimeter of a valve for blocking the paravalvular leak. More specifically, once positioned against the valve, an interior surface 450 of the first section 428 is operable to extend along an exterior surface of the stent of the valve. Meanwhile, the second section 434 is operable to extend over the perimeter of the valve and partially along an outer surface of one or more leaflets of the valve. In some embodiments, the connector element 440 may be in direct abutment with the perimeter of the valve.

In this embodiment, the first section 428 and the second section 434 have substantially the same shape, size, volume, etc., causing the occlusion device 420 to generally take on a dumbbell shape when viewed from the side. In other embodiments, the first section 428 and the second section 434 may have different sizes or shapes relative to one another. As shown, the first section 428 has an outer face 451 that is substantially circular. Similarly, the second section 434 has an outer face 452 that is substantially circular. Extending respectively from each outer face 451 and 452 are flattened central surfaces 453 and 454. As shown, the flattened central surfaces 453, 454 extend perpendicular, or substantially perpendicular from respective outer faces 451, 452. The flattened central surfaces 453, 454 may provide a better seal against the exterior surface of the valve. As further shown, the first section 428 includes a first sloped surface 455 angled towards the connector element 440, and the second section 434 includes a second sloped surface 456 angled towards the connector element 440. Each of the first and second sloped surfaces 455, 456 may be provided to channel/align the occlusion device 420 in position against the perimeter of the valve.

Figure 4B:
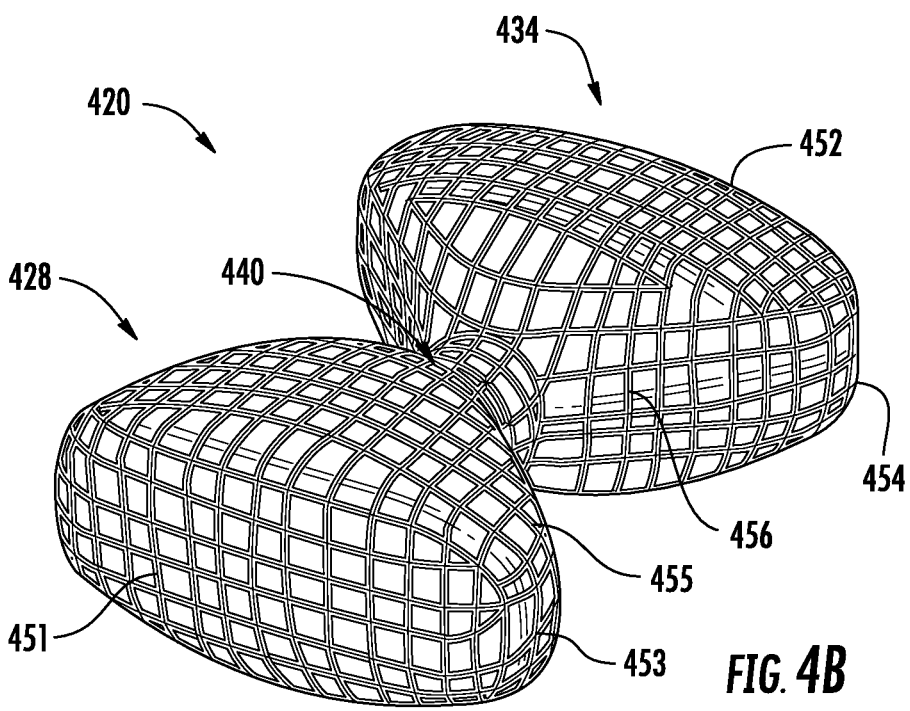

As shown in the non-limiting embodiment of FIG. 4B, the occlusion device 420 generally takes on a bow-tie shape when viewed from the top (e.g., in the orientation shown). That is, the outer face 451 of the first section 428 is substantially oval or elliptical shaped. Similarly, the outer face 452 of the second section 434 is substantially oval or elliptical shaped. Extending respectively from each outer face 451 and 452 are the flattened central surfaces 453 and 454. As shown, the flattened central surfaces 453, 454 extend perpendicular, or substantially perpendicular from respective outer faces 451, 452. The flattened central surfaces 453, 454 may provide a better seal against the exterior surface of the valve. As further shown, the first section 428 includes the first sloped surface 455 angled towards the connector element 440, and the second section 434 includes the second sloped surface 456 angled towards the connector element 440. Each of the first and second sloped surfaces 455, 456 may be provided to channel/align the occlusion device 420 in position against the perimeter of the valve.

Figure 4C:
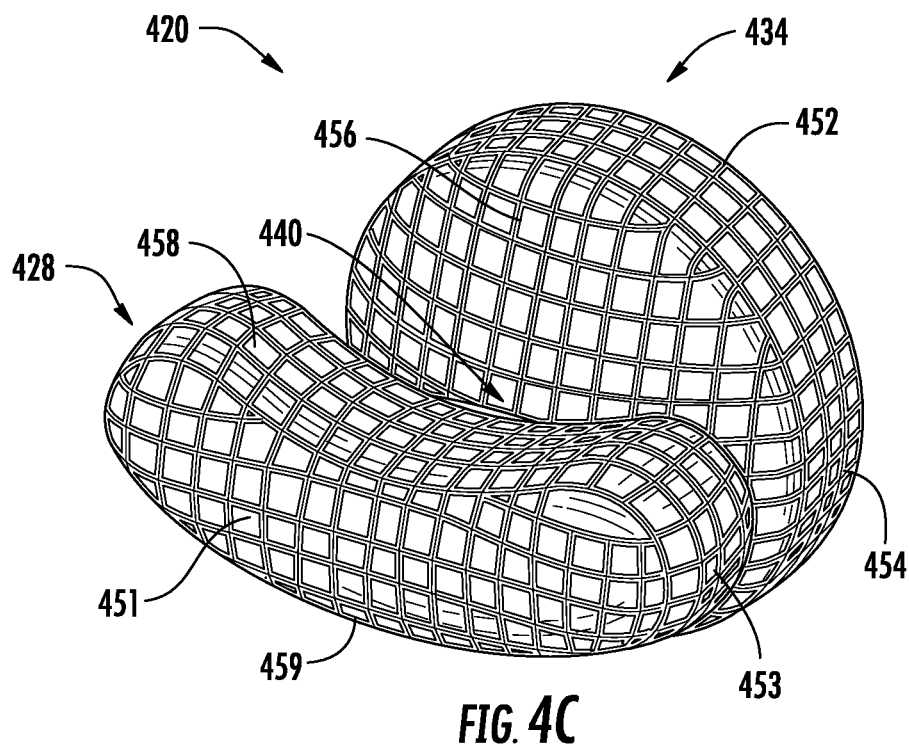

As shown in the non-limiting embodiment of FIG. 4C, the occlusion device 420 takes on a generally cufflink shape, wherein the first and second sections 428 and 434 have different shapes. That is, the outer face 451 of the first section 428 has a crescent or bean profile/shape. Meanwhile, the outer face 452 of the second section 434 is substantially circular. Extending from each outer face 451, 452 are the central surfaces 453 and 454, respectively. As shown, the central surface 453 of the first section 428 has a concave side 458 and a convex side 459. The concave side 458 may better conform to the rounded exterior surface of the stent of the valve. The central surfaces 453, 454 extend perpendicular, or substantially perpendicular from respective outer faces 451, 452. As further shown, the second section 434 includes the second sloped surface 456 extending between the flattened central surface 454 of the second section 434 and the connector element 440. In this embodiment, the second section 434 generally takes on a disc shape, which may better enable the second sloped surface 456 to extend over the leaflets of the valve.

Figure 4D:
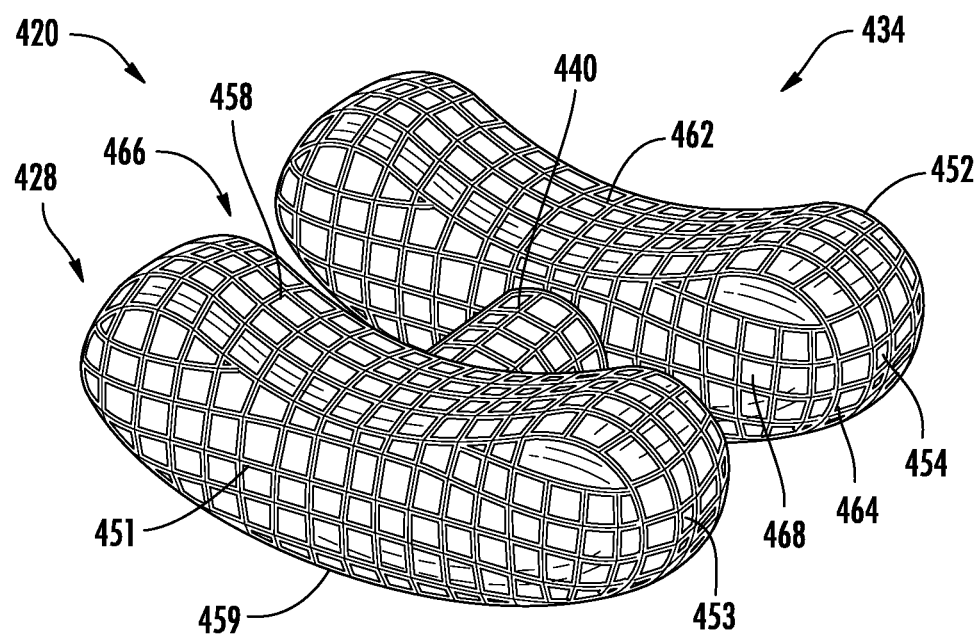

As shown in the non-limiting embodiment of FIG. 4D, the first and second sections 428 and 434 of the occlusion device 420 have generally the same shape. That is, the outer face 451 of the first section 428 has a crescent or bean profile/shape. Similarly, the outer face 452 of the second section 434 has a crescent or bean profile/shape. Extending from each outer face 451, 452 are the central surfaces 453 and 454, respectively. As shown, the central surface 453 of the first section 428 has the concave side 458 and the convex side 459, while the central surface 454 of the second section 434 has a concave side 462 and a convex side 464. Each concave side 458, 462 may be provided to better conform the occlusion device 420 to the exterior surfaces of the valve. As shown, the central surfaces 453, 454 extend perpendicular, or substantially perpendicular from respective outer faces 451, 452. The first and second sections 428 and 434 are joined by the connector element 440, which extends perpendicularly from respective inner surfaces 466, 468.

Figure 4E:
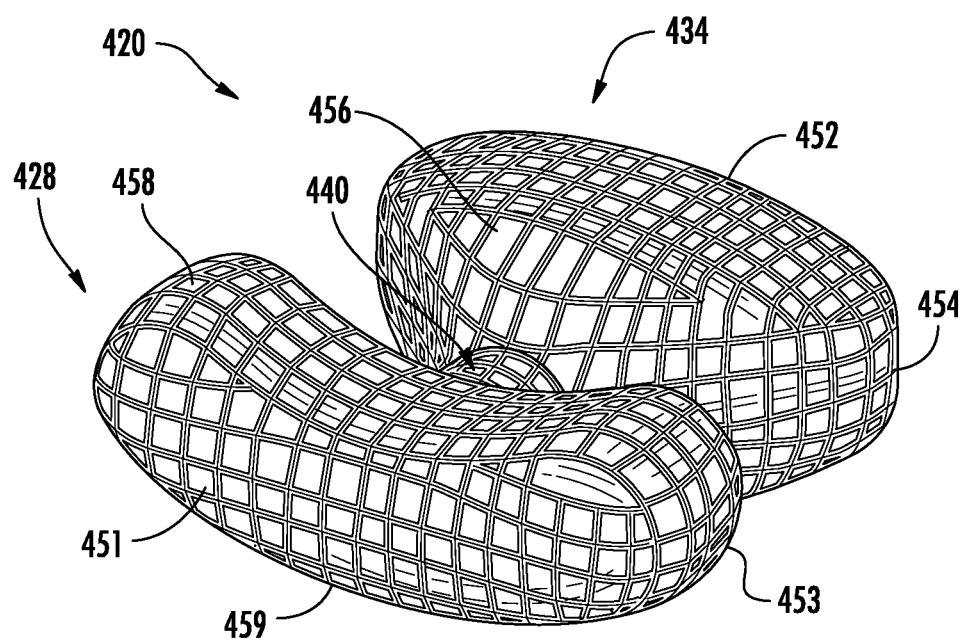

As shown in the non-limiting embodiment of FIG. 4E, the outer face 451 of the first section 428 has a crescent or bean profile/shape. Meanwhile, the outer face 452 of the second section 434 is substantially circular or oval shaped. Extending from each outer face 451, 452 are the central surfaces 453 and 454, respectively. As shown, the central surface 453 has the concave side 458 and the convex side 459. The concave side 458 may better conform to the rounded exterior surface of the stent of the valve. The central surfaces 453, 454 extend perpendicular, or substantially perpendicular, from respective outer faces 451, 452. As further shown, the second section 434 includes the second sloped surface 456 angled towards the connector element 440. The second sloped surface 456 may aid with alignment and securement of the occlusion device 420 to the valve.

Turning now to FIGS. 5A-G, various configurations of an internal frame 570 disposed within an occlusion device 520 are shown in greater detail. In some embodiments, the internal frame 570 may be solid or braided Nitinol extending through one or more of a first section 528, a second section 534, and a connector element 540 of the occlusion device 520. As shown, the internal frame 570 provides a general shape and rigidity to an outer e-spin material 572. In various embodiments, the internal frame 570 may be formed from a single piece of material (e.g., in the form of a single-filament construction or a laser-cut tube that is expanded into a desired flared shape, which is heat-set to make the flared shape the natural configuration) or formed from a plurality of frame segments (e.g., thin strands, such as wires, filaments, ribbons, and so forth) that are shaped and held together, for instance by welding, adhesives, mechanical means, and so forth, to create the internal frame 570. In general, the internal frame 570 is collapsible to fit within the lumen of the catheter.

In some embodiments, the internal frame may be radially self-expandable to an expanded unconstrained configuration, as shown, upon deployment from the catheter. The internal frame 570 may be comprised of a shape-memory material, such as from various metals and metal alloys, including nitinol (NiTi alloy) (e.g., superelastic nitinol), stainless steel, titanium, and Elgiloy (Co—Cr—Ni Alloy), among others. The internal frame 570 may also be formed from various polymers in other embodiments.

The internal frame 570 may be entirely surrounded by the outer e-spin material 572 to help promote endothelization, and to help prevent clotting due to interaction with the metal of the internal frame 570. Furthermore, in the event blood pools inside the occlusion device 520, the outer e-spin material 572 may keep clot from escaping. In various embodiments, an interior cavity defined by the outer e-spin material 572 may be filled with a biocompatible material to expand the outer e-spin material 572 into a desired shape. In other embodiments, the outer e-spin material 572 can be made over ice to obtain the desired shape.

Figure 5A:
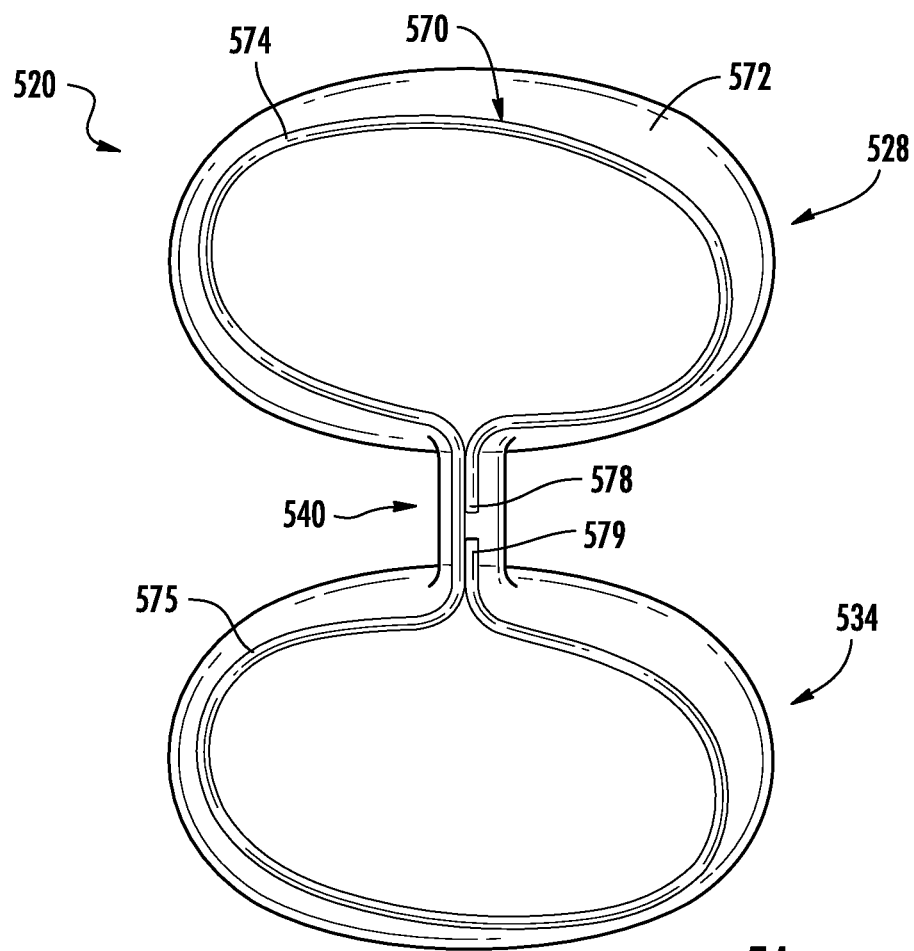
FIGS. 5A-G are perspective views illustrating various internal frames of occlusion devices according to embodiments of the present disclosure.

As shown in FIG. 5A, the internal frame 570 of the occlusion device 520 may be formed from a continuous piece of material to provide structure to the outer e-spin material 572, including a first loop 574 disposed within the first section 528 and a second loop 575 disposed within the second section 534. The internal frame 570 may extend through the connector element 540, and may include first and second ends 578 and 579, which terminate within the connector element 540. In this embodiment, the first and second loops 574, 575 are the same or similar in size and shape, and generally lie in a same plane. As a result, the first section 528 and the second section 534 take on a same or similar size and shape.

Figure 5B:
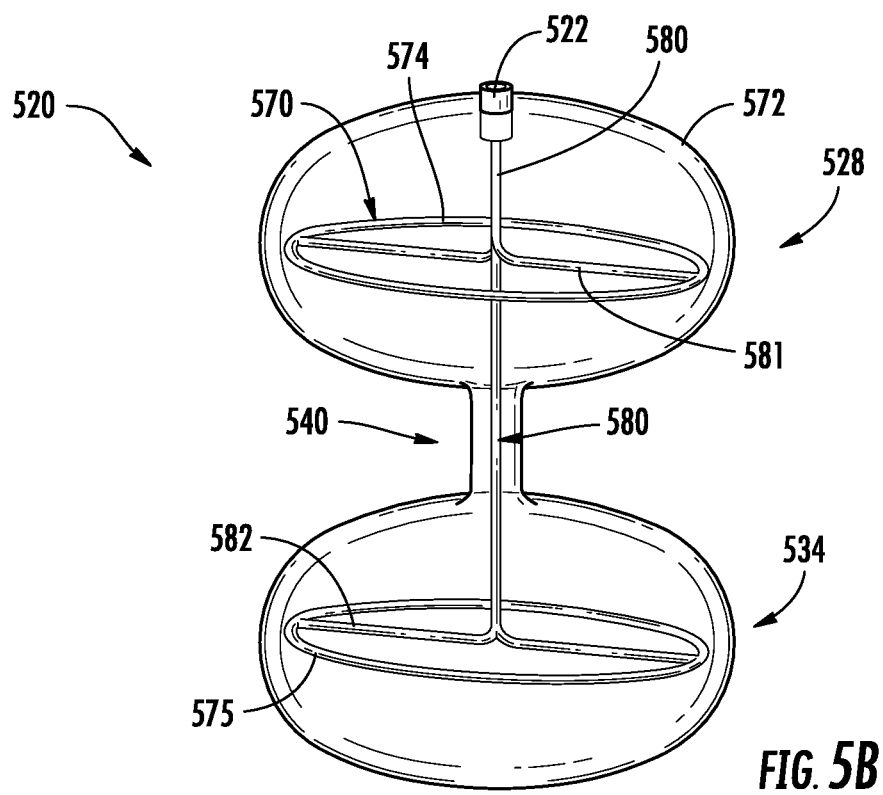

As shown in FIG. 5B, the internal frame 570 of the occlusion device 520 may be formed from a continuous piece of material to provide structure to the outer e-spin material 572, including the first loop 574 disposed within the first section 528 and the second loop 575 disposed within the second section 534. The internal frame 570 may include a center support 580 extending through the connector element 540, wherein the center support 580 connects with a crossbar 581 and a crossbar 582 of the first loop 574 and the second loop 575, respectively. In this embodiment, the first loop 574 and the second loop 575 are oriented perpendicular to the center support 580 and extend parallel to one another, along different planes. The center support 580 may extend from a connection joint 522, which is coupled to the elongate shaft (not shown) of the catheter. As shown, the connection joint 522 may be disposed partially within and partially outside of the outer e-spin material 572.

Figure 5C:
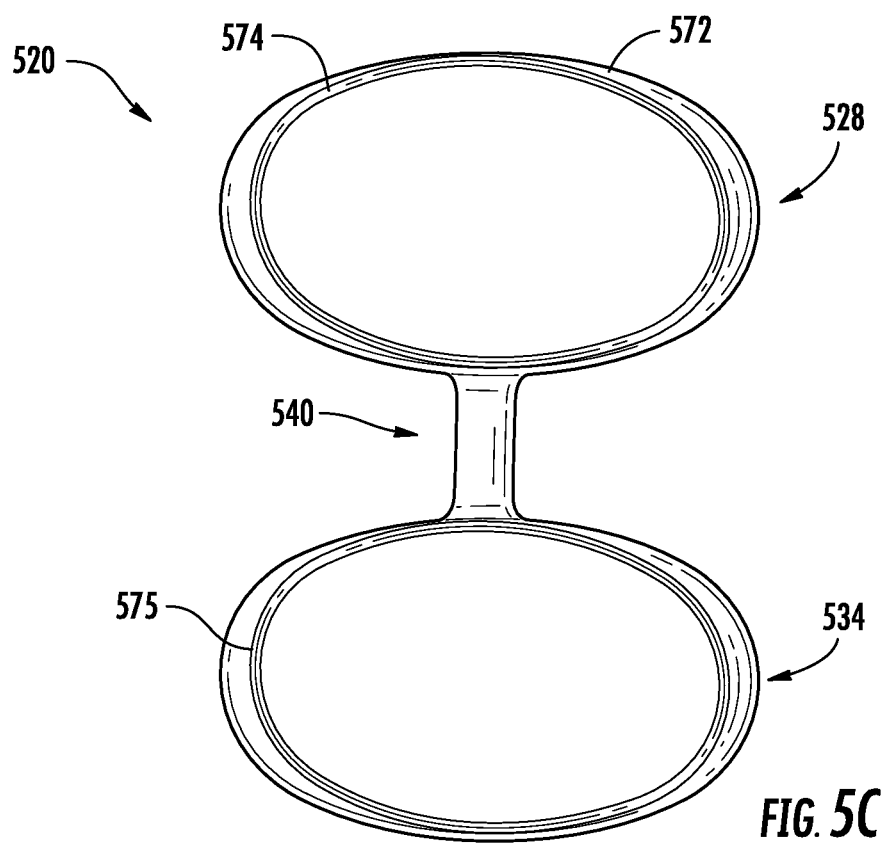

As shown in FIG. 5C, the internal frame 570 of the occlusion device 520 may include two separate pieces of material to provide structure to the outer e-spin material 572, including the first loop 574 disposed within the first section 528 and the second loop 575 disposed within the second section 534. In this embodiment, the internal frame 570 does not extend through the connector element 540. For example, the occlusion device 520 may not include a center support. As shown, the first and second loops 574, 575 may be the same or similar in size and shape, and generally lie in a same plane.

Figure 5D:
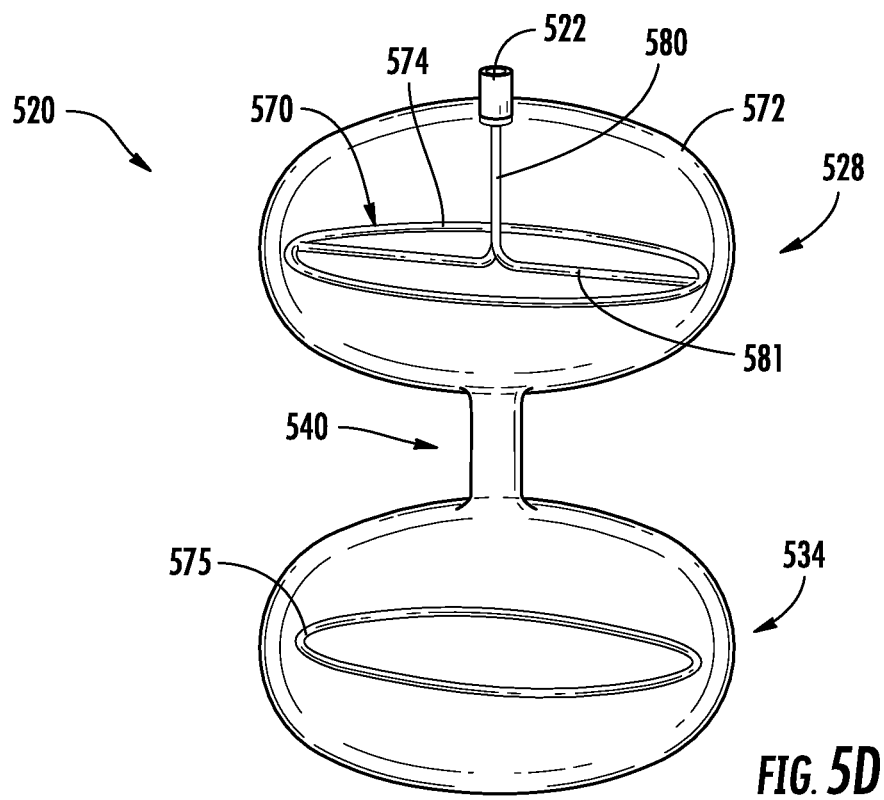

As shown in FIG. 5D, the internal frame 570 of the occlusion device 520 may include two separate pieces of material to provide structure to the outer e-spin material 572, including the first loop 574 disposed within the first section 528 and the second loop 575 disposed within the second section 534. In this embodiment, the internal frame 570 optionally may not extend through the connector element 540. As shown, the first and second loops 574, 575 may be the same or similar in size and shape, but lie in different planes that are perpendicular to one another. In this embodiment, a crossbar 581 extends longitudinally across the first loop 574, and connects with the center support 580, which is present in just the first section 528, and which is coupled to the connection joint 522.

Figure 5E:
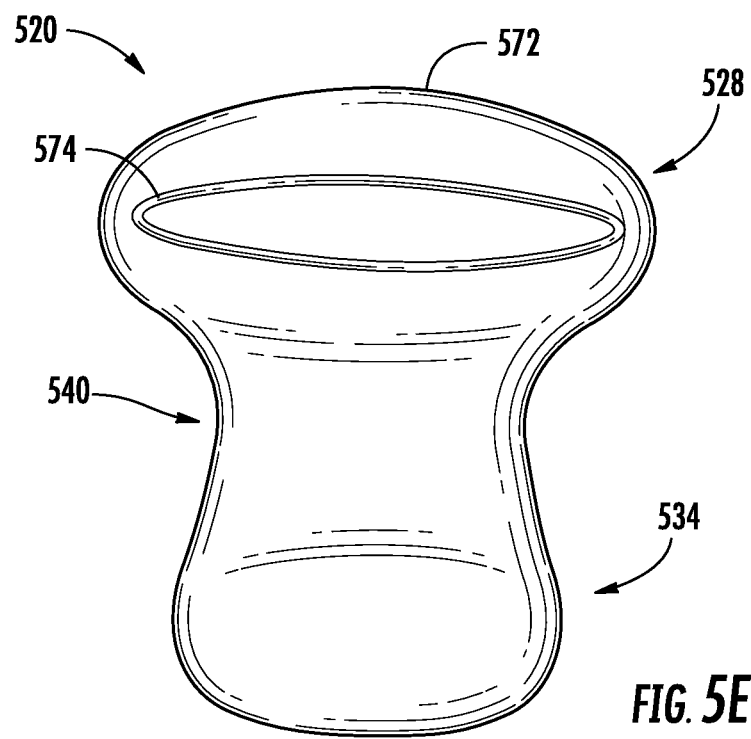

As shown in FIG. 5E, the internal frame 570 of the occlusion device 520 may include only the first loop 574 disposed within the first section 528 to provide structure to the outer e-spin material 572. In this embodiment, the internal frame 570 does not extend through the connector element 540 or into the second section 534. However, to provide support for the occlusion device 520, the diameter or thickness of the connector element 540 may be increased. As shown, in this embodiment, the diameter or thickness of the first section 528 is greater than the diameter or thickness of the second section 534.

In this embodiment, the occlusion device 520 can may be formed by filling an e-spin balloon with a biocompatible material to help hold the second section 534 open once in place within the patient. The biocompatible material could be, without limitation, a starch, a polymer, or any small material capable of being flowed into position by a fluid, such as water and/or saline. The porous material of the e-spin balloon is designed to leak the fluid, thus leaving a filled in second section 534. In other embodiments, the occlusion device 520 may not be filled with saline. Instead, the occlusion device 520 provides occlusion by folding over itself. For example, second section 534 may be permitted to fold within the patient to conform to the shape of the paravalvular leak. In yet other embodiments, the occlusion device 520 may be designed to fill with blood. The blood may clot inside the occlusion device 520, yet will not be permitted to escape, thus aiding with endothelization.

Figure 5F:
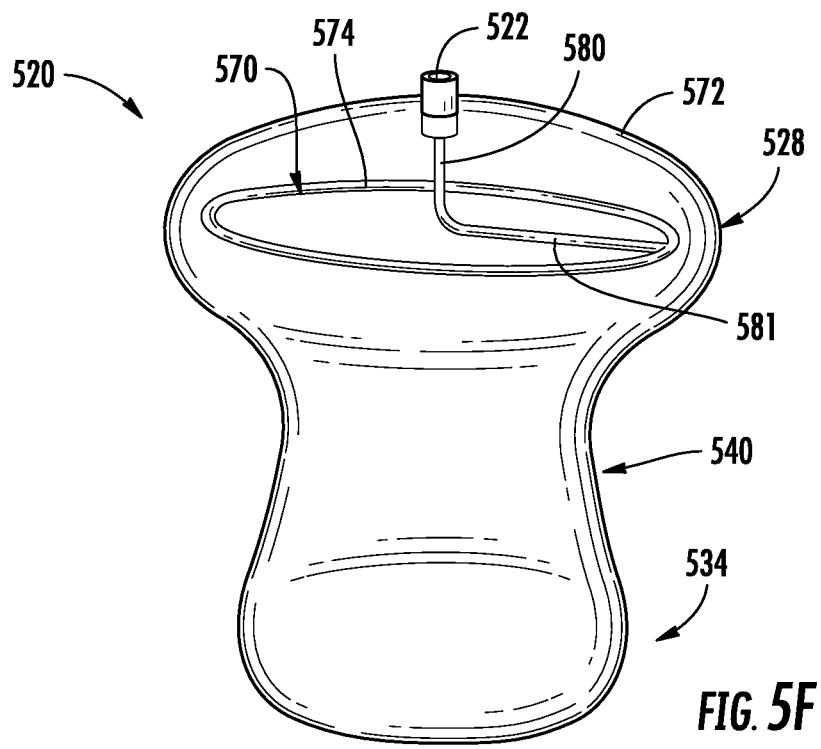

As shown in FIG. 5F, the internal frame 570 of the occlusion device 520 may include only the first loop 574 disposed within the first section 528 to provide structure to the outer e-spin material 572. In this embodiment, the internal frame 570 does not extend through the connector element 540 or into the second section 534. The first loop 574 includes the crossbar 581 extending radially and connecting with the center support 580, which is provided in only the first section 528, and which couples to the connection joint 522. Furthermore, the diameter or thickness of the connector element 540 is closer to that of the diameter or thickness of first section 528 and the second section 534. As shown, in this embodiment, the diameter or thickness of the first section 528 is greater than the diameter or thickness of the second section 534. In some embodiments, the first section 528 and/or the second section 534 may be filled with saline or blood once in place.

Figure 5G:
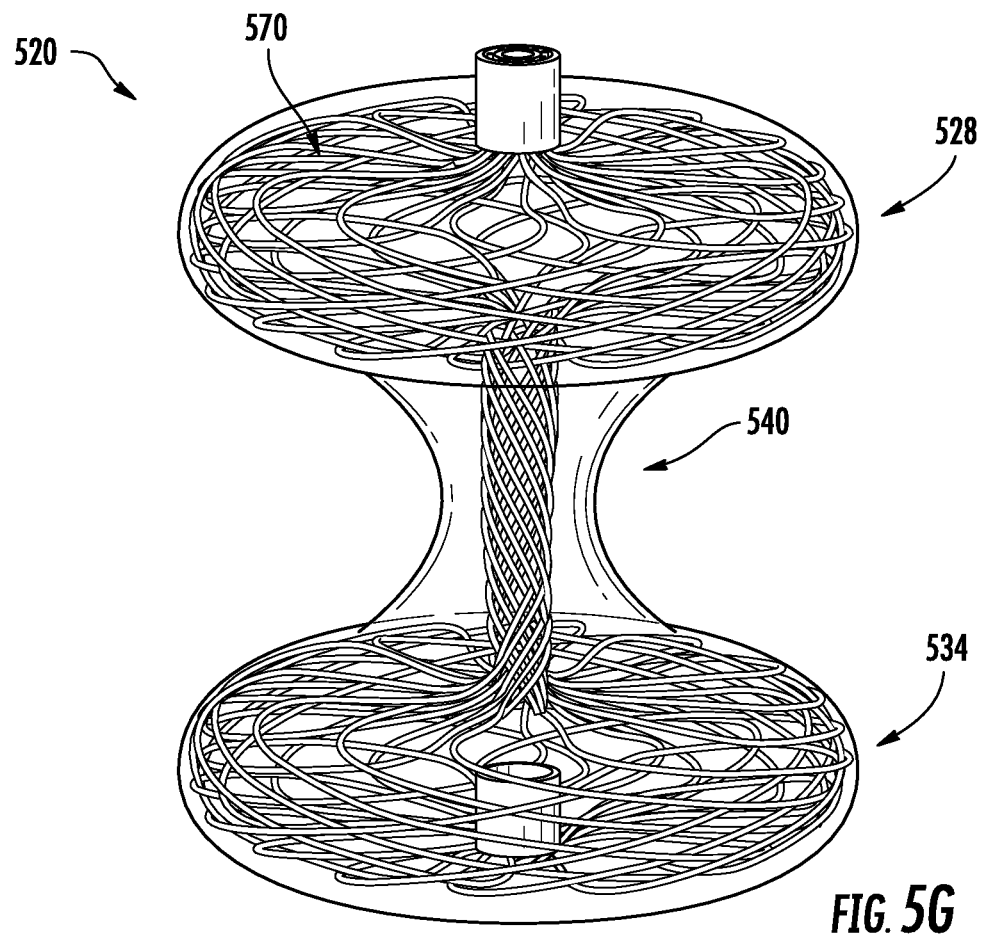

As shown in FIG. 5G, the internal frame 570 of the occlusion device 520 may be a braided frame extending through the first section 528, the second section 534, and the connector element 540. In this embodiment, the internal frame 570 may have two or more strands of material wound in a helical fashion. The braiding of such material in this fashion may result in crossed or lattice structure. As can be understood, the dimension of the lattice and the formed interstices is determined, at least in part, by the thickness of the strand materials, the number of strands and the number of helices per unit length of the internal frame 570. As shown, the braided internal frame 570 through the connector element 540 is more densely or tightly wound than the braided frame in the first and second sections 528, 534. The outer e-spin material 572 of the occlusion device 520 generally takes on the shape of the braided internal frame 570.

Figure 6:
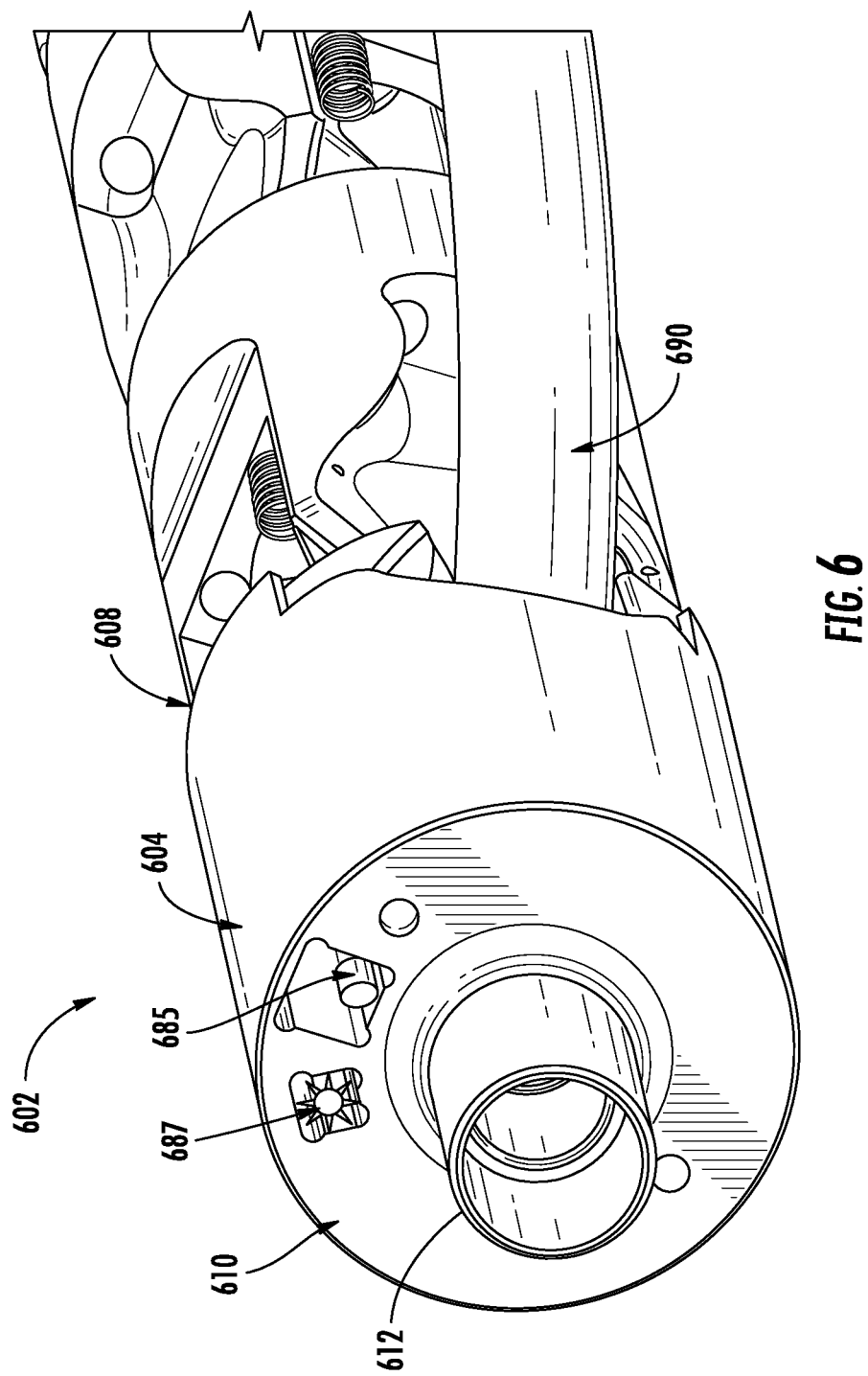
FIG. 6 is a perspective view of a portion of the catheter of the apparatus of FIG. 1 according to embodiments of the present disclosure.

Turning now to FIG. 6, a portion of the catheter 602 will be described in greater detail. As shown, the distal end 610 of the main body 604 of the catheter 602 includes openings for a visualization element 685 (e.g., a camera), one or more lighting elements (e.g., a LED light) 687, and a saline spray (not shown). In a central area of the distal end 610 of the main body 604 is the working channel 612, which is operable to contain the elongate shaft (not shown) used to deliver the occlusion device(s). In some embodiments, the visualization element 685 and the lighting element 687 may be housed inside the balloon (FIGS. 1-2) and may communicate with an external computer system, such as a lighting and imaging system, imaging processing console, etc. Positioning the lighting element 687 inside the balloon may supplement an external light source or may eliminate the need for an external light source. Moreover, by putting the lighting element 687 within the balloon, wider angles of illumination may be achieved.

In some embodiments, the visualization element 685 is an integrated camera providing visual imaging of a patient's anatomy before, during, and after delivery of the occlusion device. The visualization element 685 may be fully or partially disposed within a lumen defined by the tubular shape of the main body 604. The visualization element 685 can be coupled to electrical and/or optical cables 690 that extend longitudinally through the main body 604 between the distal end 610 and the proximal end 608. In some cases, the visualization element 685 is electrically connected to external electronics via wires through the lumen. For example, in some cases, a bundle of fiber optic cables, each with their own lens (e.g., borescopes), can be connected to an eyepiece for viewing and/or to a camera for electrical conversion and transfer to a screen. In some cases, the visualization element 685 operates with externally powered but internal lighting elements 687 to emit light so that the tissue can be seen.

During use, the catheter 602 may be brought into a desired position using feedback from the visualization element 685 to align the working channel 612 with the location of the paravalvular leak. The occlusion device (not shown) may then be delivered from the working channel 612, into an area for plugging the paravalvular leak. One or more additional occlusion devices may be similarly deployed depending upon the size and location(s) of the leak(s). Once in place, the position of the occlusion device(s) may then be verified using the visualization element 685.

Figure 7:
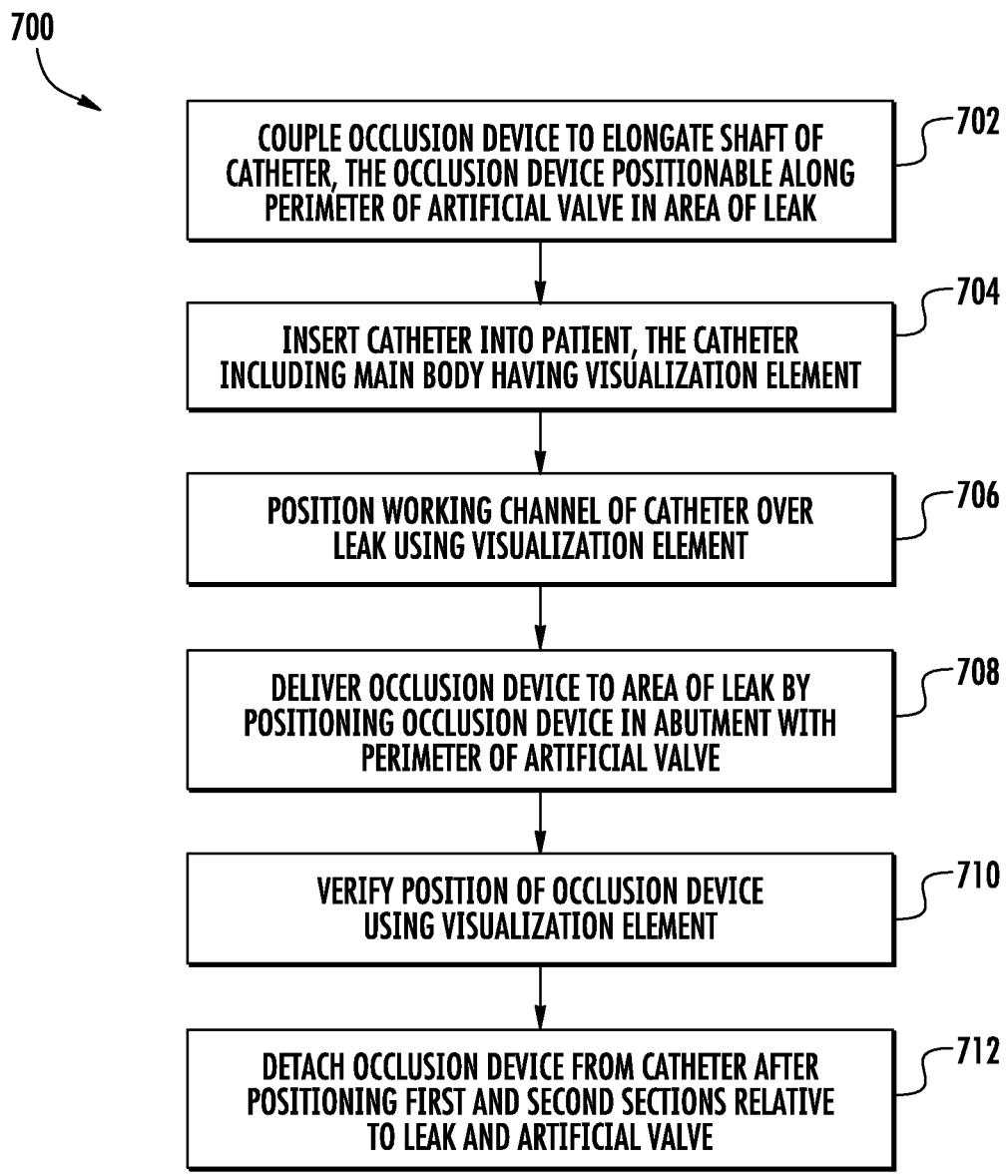
FIG. 7 depicts a process for delivering an occlusion device to a paravalvular leak from a catheter according to embodiments of the present disclosure.

Turning now to FIG. 7, a method 700 for delivering an occlusion device to a paravalvular leak according to embodiments of the disclosure will be described in greater detail. At block 702, the method 700 may include coupling one or more occlusion devices to an elongate shaft of a catheter, wherein each occlusion device includes first and second sections positionable along a perimeter of a prosthetic valve in an area of a paravalvular leak. In some embodiments, the occlusion device includes a leading end including the first section, and a trailing end opposite the leading end, the trailing end including the second section. In some embodiments, the occlusion device further includes a connector element extending between the first and second sections, wherein the connector element is operable to abut or engage a perimeter of a prosthetic valve. In some embodiments, a diameter length of the connector element is less than a diameter length of the first section or the second section of the occlusion device.

In some embodiments, the occlusion device may include a covering material, which may be made from an electrospun material (e.g., chronoflex, PIB PUR, PVDF, PCL, or PLGA) to help with endothelialization over the occlusion device and impede blood flow back into the atrium. In some embodiments, the first and second sections of the occlusion device have one of the following shapes: circular, elliptical, square, and crescent. In some embodiments, a shape of the first section of the occlusion device is different than a shape of the second section of the occlusion device. In some embodiments, the first section of the occlusion device has an interior concave surface operable to abut an exterior surface of a stent of the artificial valve. In some embodiments, the second section of the occlusion device is operable to extend over the perimeter of the artificial valve and partially along an outer surface of one or more leaflets of the artificial valve.

In some embodiments, the method may include providing an internal frame of the occlusion device, the internal frame being connected to a connection joint extending from the second section, wherein the connection joint is coupled with the elongate shaft of the catheter. In some embodiments, the internal frame is disposed within at least one of: the first section, the second section, and the connector element. In some embodiments, the internal frame is a shape-memory material, such as Nitinol. In some embodiments, the internal frame is a braided frame.

At block 704, the method 700 may include inserting the catheter within a patient, the catheter including a main body having a visualization element disposed in a distal end of the main body. In some embodiments, the catheter further includes a working channel extending from the distal end of the main body, and the elongate shaft, which is extendable from the working channel.

At block 706, the method 700 may include positioning the working channel of the catheter over the paravalvular leak using the visualization element. In some embodiments, the visualization element is an integrated camera providing visual feedback. The visualization element may be fully or partially disposed within a lumen defined by the tubular shape of the main body of the catheter. The visualization element can be coupled to electrical and/or optical cables that extend longitudinally through the main body of the catheter.

At block 708, the method 700 may include delivering the occlusion device to the paravalvular leak by positioning the occlusion device in abutment with the perimeter of the prosthetic valve. In some embodiments, the method may include positioning an interior concave surface of the first section of the occlusion device directly against an exterior surface of a stent of the artificial valve, and positioning the second section of the occlusion device partially over an outer surface of one or more leaflets of the artificial valve.

Once in place, at block 710, the method 700 may include verifying the position of occlusion device using the visualization element. If positioning is satisfactory, at block 712, the method 700 may include detaching the occlusion device from the catheter after positioning of the first and second sections relative to the paravalvular leak and the artificial valve. It will be appreciated that to insert additional occlusion devices, as desired, any or all of blocks 702, 704, 706, 708, 710, and 712 may be repeated.

It should be noted that the methods described herein, including the method 700 illustrated in FIG. 7, are not required to be executed in the order described, or in any particular order. Moreover, various activities described with respect to the methods identified herein can be executed in serial or parallel fashion.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Furthermore, as used herein, the term "proximal," when used in connection with a prosthetic heart valve and the catheter herein, refers to the end of the main body of the catheter farthest from the heart when the catheter is inserted into a patient, whereas the term "distal," when used in connection with a prosthetic heart valve and the catheter, refers to the end of the main body of the catheter closest to the heart when the catheter is inserted into a patient. When used in connection with devices for delivering a prosthetic heart valve or other medical device into a patient, the terms "trailing" and "leading" are to be taken as relative to the user of the delivery devices. "Trailing" is to be understood as relatively close to the user, and "leading" is to be understood as relatively farther away from the user.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A paravalvular occlusion apparatus, comprising:
  a catheter comprising:
    a main body having a proximal end and a distal end;
    a visualization element disposed in the distal end of the main body;
    a working channel extending from the distal end of the main body; and
    an elongate shaft extendable from the working channel; and
  an occlusion device coupled to the elongate shaft, the occlusion device comprising:
    a leading end including a first section; and a trailing end opposite the leading end, the trailing end including a second section having a different size or shape from the first section;

wherein the first section and the second section are operable to be positioned along an exterior perimeter of an artificial valve.

2. The paravalvular occlusion apparatus of claim 1, the occlusion device further comprising a connector element extending between the first and second sections.

3. The paravalvular occlusion apparatus of claim 2, wherein a diameter length of the connector element is less than a diameter length of at least one of the first section, or the second section.

4. The paravalvular occlusion apparatus of claim 2, the occlusion device further comprising an internal frame disposed within at least one of: the first section, the second section, or the connector element.

5. The paravalvular occlusion apparatus of claim 4, wherein the internal frame is a braided or laser cut frame of a shape-memory material extending throughout the first section, the second section, and the connector element.

6. The paravalvular occlusion apparatus of claim 4, wherein the internal frame of the occlusion device is connected to a connection joint extending from the second section, wherein the connection joint is coupled with the elongate shaft of the catheter.

7. The paravalvular occlusion apparatus of claim 1, the catheter further comprising a balloon extending around the working channel.

8. The paravalvular occlusion apparatus of claim 1, wherein the first and second sections of the occlusion device have one of the following shapes:
circular, elliptical, square, or crescent.

9. The paravalvular occlusion apparatus of claim 1, wherein the first section of the occlusion device has an interior concave surface configured and operable to abut an exterior surface of a stent of the artificial valve.

10. The paravalvular occlusion apparatus of claim 1, wherein the second section of the occlusion device is configured and operable to extend over the exterior perimeter of the artificial valve and partially along an outer surface of one or more leaflets of the artificial valve.

11. The paravalvular occlusion apparatus of claim 1, further comprising one or more additional occlusion devices positionable along the perimeter of the artificial valve.

12. The paravalvular occlusion apparatus of claim 11, wherein the occlusion device is in direct physical abutment with the one or more additional occlusion devices.

13. A paravalvular occlusion apparatus, comprising:
a catheter comprising:
a main body having a proximal end and a distal end;
a visualization element disposed in the distal end of the main body;
a working channel extending from the distal end of the main body; and
an elongate shaft extendable from the working channel; and
an occlusion device coupled to the elongate shaft, the occlusion device comprising:
a leading end including a first section;
a trailing end opposite the leading end, the trailing end including a second section; and
a connector element extending between the first and second sections and having a diameter smaller than the diameters of the first and second sections;

wherein the first section and the second section and the connector element are configured and operable to be positioned along an exterior perimeter of an artificial valve in an area of a paravalvular leak.

14. The paravalvular occlusion apparatus of claim 13, the occlusion device further comprising an expandable internal frame disposed within at least one of: the first section, the second section, or the connector element.

15. A method for delivering an occlusion device to a paravalvular leak, the method comprising:
advancing a catheter in a body of patient to a para valvular leak, the catheter comprising:
a main body having a proximal end and a distal end;
a visualization element disposed in the distal end of the main body;
a working channel extending from the distal end of the main body; and
an elongate shaft extendable from the working channel; and
delivering an occlusion device from the working channel of the catheter to the exterior perimeter of a prosthetic valve, the occlusion device comprising:
a leading end including a first section; and
a trailing end opposite the leading end, the trailing end including a second section connected to the first section by a connector element differentiating the first and second sections, wherein the first section and the second section and the connector element are operable to be positioned along an exterior perimeter of the prosthetic valve.

16. The method of claim 15, further comprising:
positioning the working channel over the paravalvular leak using the visualization element; deploying the occlusion device to the paravalvular leak by positioning the occlusion device in abutment with the perimeter of the prosthetic valve; and
verifying a position of the occlusion device using the visualization element.

17. The method of claim 16, further comprising:
positioning an interior concave surface of the first section of the occlusion device directly against an exterior surface of a stent of the prosthetic valve;
positioning the second section of the occlusion device partially over an outer surface of one or more leaflets of the prosthetic valve; and
detaching the occlusion device from the catheter after positioning of the first and second sections relative to the prosthetic valve.

18. The method of claim 15, further comprising positioning one or more additional occlusion devices along the perimeter of the prosthetic valve.

19. The paravalvular occlusion apparatus of claim 13, wherein the connector element is capable of being in direct abutment with the exterior perimeter of the artificial valve.

20. The paravalvular occlusion apparatus of claim 2, wherein the connector element has a different diameter than the diameters of the first and second sections.

* * * * *